(12) United States Patent
Botich et al.

(10) Patent No.: US 7,527,607 B2
(45) Date of Patent: May 5, 2009

(54) HYPODERMIC SYRINGE WITH RETRACTABLE NEEDLE

(75) Inventors: Michael J. Botich, Oxnard, CA (US); Thor R. Halseth, Agoura, CA (US); John Barker, Ventura, CA (US)

(73) Assignee: MDC Investment Holdings, Inc., Wilmington, DE (US)

( * ) Notice: Subject to any disclaimer, the term of this patent is extended or adjusted under 35 U.S.C. 154(b) by 0 days.

(21) Appl. No.: 10/220,767

(22) PCT Filed: Mar. 6, 2001

(86) PCT No.: PCT/US01/06977

§ 371 (c)(1), (2), (4) Date: Dec. 2, 2002

(87) PCT Pub. No.: WO01/66179

PCT Pub. Date: Sep. 13, 2001

(65) Prior Publication Data

US 2003/0208164 A1 Nov. 6, 2003

(51) Int. Cl.
*A61M 5/00* (2006.01)
(52) U.S. Cl. .................................................. 604/110
(58) Field of Classification Search ................. 604/110, 604/187, 192, 194, 198, 220, 125, 129, 158, 604/162, 164.01, 197; 128/919
See application file for complete search history.

(56) References Cited

U.S. PATENT DOCUMENTS

| | | | |
|---|---|---|---|
| 2,876,770 A | 3/1959 | White | |
| 3,306,290 A | 2/1967 | Weltman | |
| 3,463,152 A | 8/1969 | Sorenson | |
| 3,658,061 A | 4/1972 | Hall | |
| 3,890,971 A | 6/1975 | Leeson et al. | |
| 4,026,287 A | 5/1977 | Haller | |
| 4,333,457 A | 6/1982 | Margulies | |
| 4,378,015 A | 3/1983 | Wardlaw | |
| 4,392,859 A | 7/1983 | Dent | |
| 4,425,120 A | 1/1984 | Sampson et al. | |
| 4,507,117 A | 3/1985 | Vining et al. | |
| 4,507,118 A | 3/1985 | Dent | |
| 4,542,749 A | 9/1985 | Caselgrandi et al. | |
| 4,573,976 A | 3/1986 | Sampson et al. | |
| 4,592,744 A | 6/1986 | Jagger et al. | |
| 4,631,057 A | 12/1986 | Mitchell | |
| 4,664,654 A | 5/1987 | Strauss | |

(Continued)

*Primary Examiner*—Kevin C Sirmons
*Assistant Examiner*—Elizabeth R MacNeill
(74) *Attorney, Agent, or Firm*—Stoel Rives LLP

(57) ABSTRACT

A safety needle-bearing medical advice (10) is provided. Specifically, a safety device for injecting medicinal fluid into a patient is provided. The device comprises a hollow housing (20), a needle assembly (40) and a plunger (30). The needle assembly (40) releasably retains a needle (43) in an extended position in which the sharpened tip of the needle is exposed for use. At the end of an injection stroke, the plunger (30) engages the needle assembly (40), such that the needle (43) is released and retracted into a cavity (38) within the plunger. The device (10) includes structure for reducing the dead-space volume, which represents the amount a fluid remaining in the device at the end of an injection stroke. In addition, preferably the device (10) includes structure for minimizing the volume of potential air bubbles trapped in the medicinal fluid prior to an injection.

24 Claims, 6 Drawing Sheets

U.S. PATENT DOCUMENTS

| | | | |
|---|---|---|---|
| 4,675,005 A | 6/1987 | DeLuccia | |
| 4,692,156 A | 9/1987 | Haller | |
| 4,710,170 A | 12/1987 | Haber et al. | |
| 4,723,943 A | 2/1988 | Spencer | |
| 4,725,267 A | 2/1988 | Vaillancourt | |
| 4,737,144 A | 4/1988 | Choksi | |
| 4,747,831 A | 5/1988 | Kulli | |
| 4,767,413 A | 8/1988 | Haber et al. | |
| 4,770,655 A | 9/1988 | Haber et al. | |
| 4,804,371 A | 2/1989 | Vaillancourt | |
| 4,813,426 A | 3/1989 | Haber et al. | |
| 4,828,548 A | 5/1989 | Walter | |
| 4,838,863 A | 6/1989 | Allard et al. | |
| 4,838,869 A | 6/1989 | Allard | |
| 4,850,968 A | 7/1989 | Romano | |
| 4,863,435 A | 9/1989 | Sturman et al. | |
| 4,874,382 A | 10/1989 | Lindemann et al. | |
| 4,887,998 A | 12/1989 | Martin et al. | |
| 4,894,055 A | 1/1990 | Sudnak | |
| 4,898,589 A | 2/1990 | Dolgin et al. | |
| 4,900,307 A | 2/1990 | Kulli | |
| 4,906,236 A | 3/1990 | Alberts et al. | |
| 4,911,693 A | 3/1990 | Paris | |
| 4,917,673 A | 4/1990 | Coplin | |
| 4,921,486 A | 5/1990 | DeChellis et al. | |
| 4,927,414 A | 5/1990 | Kulli | |
| 4,927,416 A | 5/1990 | Tomkiel | |
| 4,929,237 A | 5/1990 | Medway | |
| 4,932,947 A | 6/1990 | Cardwell | |
| 4,946,446 A | 8/1990 | Vadher | |
| 4,955,868 A | 9/1990 | Klein | |
| 4,955,869 A | 9/1990 | Bin | |
| 4,955,870 A | 9/1990 | Ridderheim et al. | |
| 4,966,592 A | 10/1990 | Burns et al. | |
| 4,966,593 A | 10/1990 | Lennox | |
| 4,973,316 A | 11/1990 | Dysarz | |
| 4,988,339 A | 1/1991 | Vadher | |
| 4,994,034 A | 2/1991 | Botich et al. | |
| 5,017,187 A | 5/1991 | Sullivan | |
| 5,019,044 A | 5/1991 | Tsao | |
| 5,046,508 A | 9/1991 | Weissler | |
| 5,049,133 A * | 9/1991 | Villen Pascual | 604/110 |
| 5,053,010 A | 10/1991 | McGary et al. | |
| 5,064,419 A | 11/1991 | Gaarde | |
| 5,084,018 A | 1/1992 | Tsao | |
| 5,129,884 A | 7/1992 | Dysarz | |
| 5,180,370 A * | 1/1993 | Gillespie | 604/110 |
| 5,188,599 A | 2/1993 | Botich et al. | |
| 5,211,629 A | 5/1993 | Pressly et al. | |
| 5,318,536 A * | 6/1994 | Williams | 604/110 |
| 5,407,431 A | 4/1995 | Botich et al. | |
| 5,685,863 A | 11/1997 | Botich et al. | |
| 5,788,677 A | 8/1998 | Botich et al. | |
| 5,800,395 A | 9/1998 | Botich et al. | |
| 6,096,005 A | 8/2000 | Botich et al. | |
| 6,179,812 B1 | 1/2001 | Botich et al. | |
| 6,673,044 B2 * | 1/2004 | Righi et al. | 604/110 |

* cited by examiner

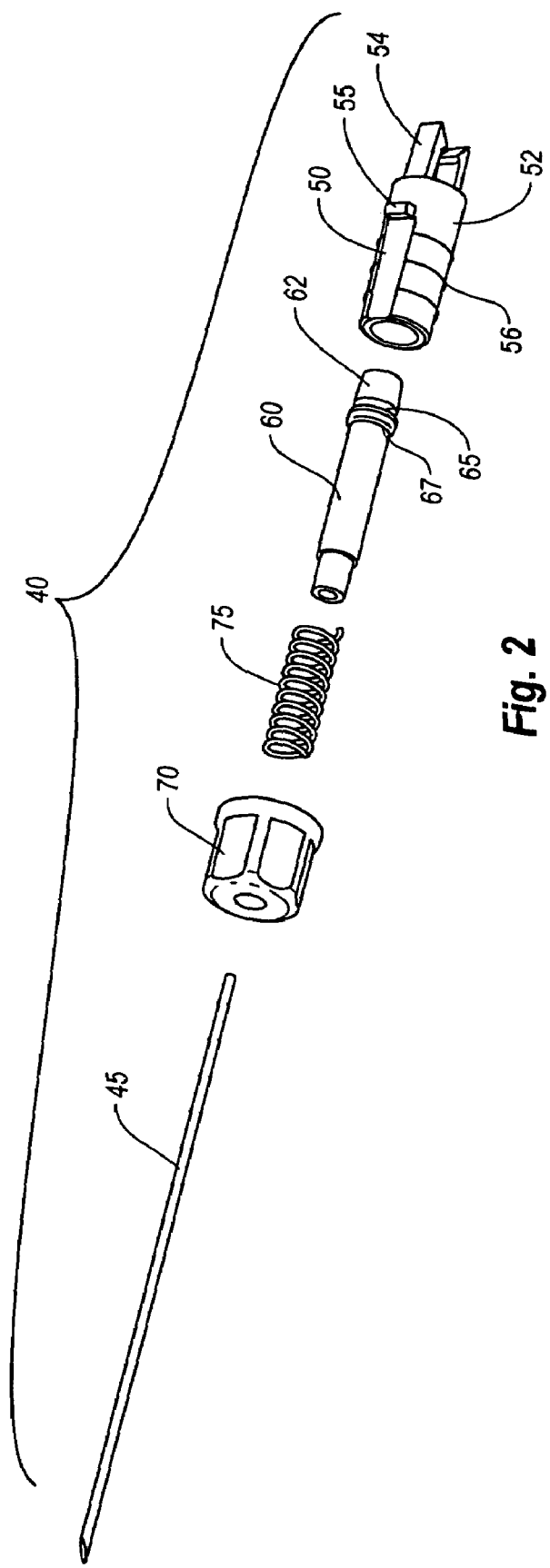
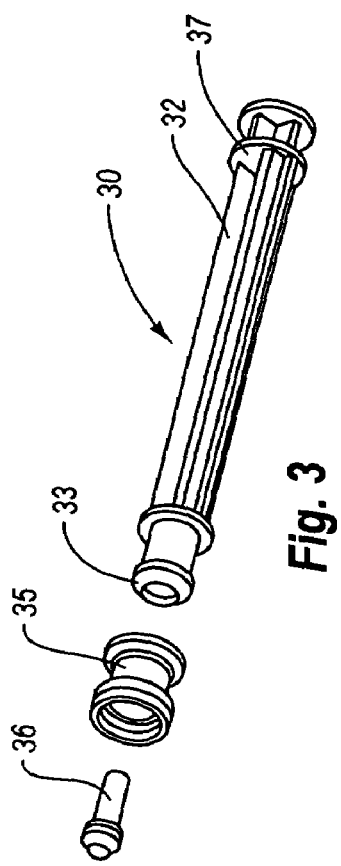
Fig. 2
Fig. 3

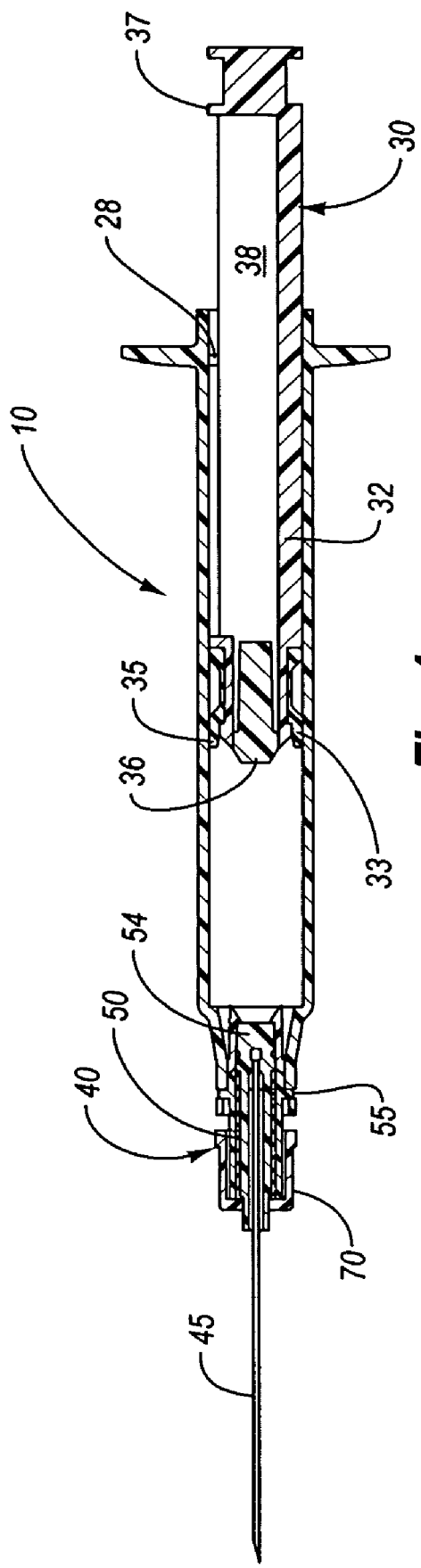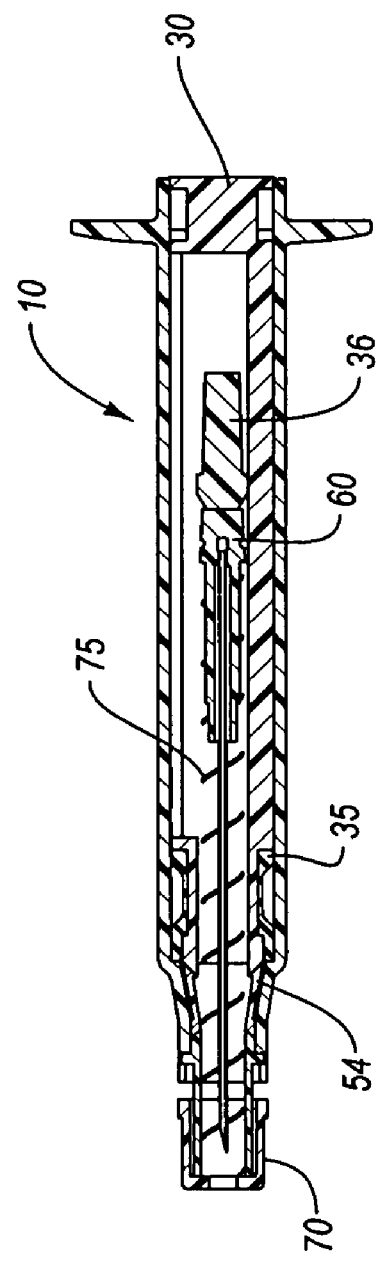
Fig. 4
Fig. 5

HYPODERMIC SYRINGE WITH RETRACTABLE NEEDLE

FIELD OF THE INVENTION

The present invention relates to syringes for administering injections of medicinal fluids to a patient or withdrawal of fluid, such as blood from a patient. More specifically, the invention relates to such devices having a retractable needle feature for rendering the device non-reusable and safely disposable.

BACKGROUND OF THE INVENTION

Various types of medical devices employ a needle for piercing the skin of a patient for diagnostic or therapeutic purposes. One such device is a hypodermic syringe. Handling of such needle-bearing medical devices after the needle is withdrawn from the patient can result in transmission of various pathogens, most notably human immune virus (HIV), to uninfected medical personnel, due to an inadvertent needle stick. Accordingly, it is desirable to provide a device for injecting medication or withdrawing fluid, wherein the needle is retracted into the housing of the device after use.

The following detailed description of the preferred embodiments will be better understood when read in conjunction with the figures, in which:

FIG. 2 is an exploded perspective view of a needle subassembly of the syringe illustrated in FIG. 1;

FIG. 3 is an exploded perspective view of a plunger subassembly of the syringe illustrated in FIG. 1;

FIG. 4 is a cross-sectional view of the syringe illustrated in FIG. 1;

FIG. 5 is a cross-sectional view of the syringe illustrated in FIG. 4, showing the needle in a retracted position;

DETAILED DESCRIPTION OF THE PREFERRED EMBODIMENTS

Figure 1:
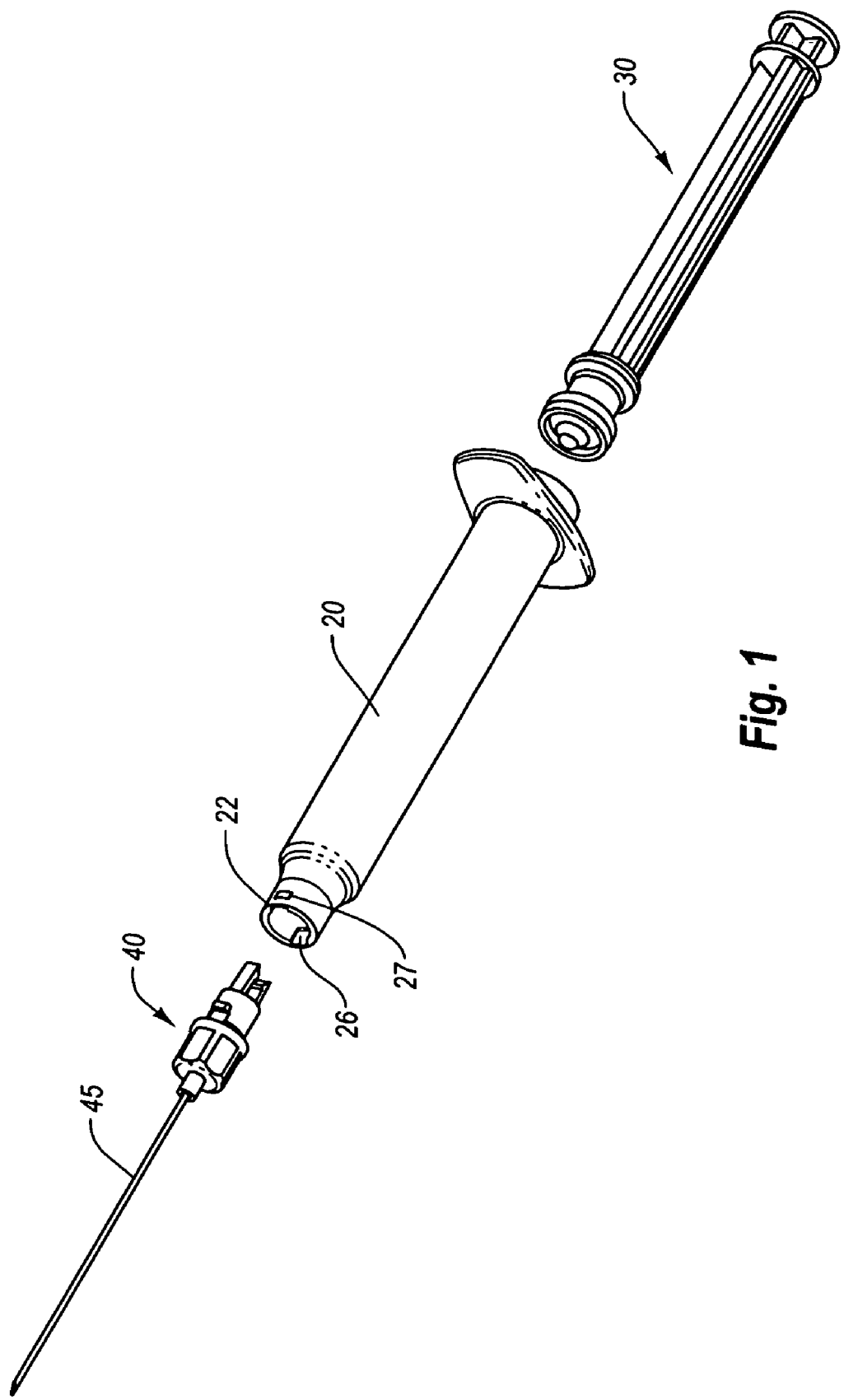
FIG. 1 is an exploded perspective view of a safety hypodermic syringe having a retractable needle, manifesting aspects of the present invention.

Referring now to the figures in general, and more specifically to FIG. 1, a retractable needle safety hypodermic syringe is designated generally 10. The syringe 10 includes a barrel 20, a plunger 30 reciprocally displaceable within the barrel, and a needle assembly 40 attachable to the forward end of the barrel. The needle assembly releasably retains a needle 45, such that after use, the needle is retracted into the barrel 20, so that the needle is shielded after use to prevent inadvertent contact with the contaminated needle after use.

The barrel is a generally hollow cylinder having a tip 22 configured to cooperate with the needle assembly 40. The rearward end of the barrel is generally open for receiving the plunger 30. The plunger 30 is reciprocally displaceable within the barrel for drawing fluid into the barrel or expelling fluid from the barrel.

The plunger 30 comprises a substantially rigid elongated plunger rod 32 and a piston 35 attached to the forward end of the plunger rod 32. The piston 35 forms a fluid tight seal with the interior surface of the barrel 20. As discussed further below, the piston 35 is axially compressible at the end of the injection stroke to reduce the dead space at the forward end of the barrel. Dead space refers to the volume in the barrel in which a fluid can reside at the end of an injection stroke. Effectively, the dead space volume of a syringe is the amount of medication that is wasted because the fluid in the dead space cannot be injected.

The forward end or head 33 of the plunger rod 32 is configured to matingly engage the needle assembly 40. In the present instance, the plunger head 33 is substantially frustoconical. The plunger rod 32 is hollow, having a cavity 38 for receiving the needle 45 after retraction. The plunger head 33 has an opening or orifice through which the needle passes into the cavity 38 during retraction. This orifice is sealed by a displaceable plug 36. The plunger rod may be a substantially hollow cylinder. However in the present instance, the plunger rod 32 generally U-shaped channel having an opened top edge as shown in FIGS. 4 and 5. The plunger rod further comprises a circumferential flange 37 adjacent the rearward end wall of the cavity 38. The flange 37 is a locking element that mates with an annular rib 28 that protrudes inwardly from the inner surface of the barrel 20. The locking flange 37 and the locking rib 28 lock the plunger 30 against rearward displacement at the end of an injection stroke. Specifically, as the plunger 30 is displaced forwardly, the locking flange 37 rides over the rearward face of the locking rib 28, which is tapered. The forward face of the locking rib 28 forms a substantially square shoulder that cooperates with the flange 37 to impede rearward displacement of the plunger 30.

Referring now to FIG. 2, the details of the needle assembly 40 are most clearly seen. The needle assembly 40 includes the needle 45, a spring 75 biasing the needle rearwardly, a needle retainer 50 releasably retaining the needle against the bias of the spring, a needle fitting 60 attached to the rearward end of the needle to provide an engagement surface for the needle retainer, and a cap 70 enclosing the forward end of the needle assembly.

The needle retainer 50 comprises a pair of radially deformable axially elongated fingers 54 extending rearwardly from a substantially cylindrical body 52. The rearward portion of the cylindrical body 52 is configured to form an interference fit with the interior of the tip 22 of the barrel 20. In this way, a fluid tight seal, as indentified in FIG. 6 at "A", is formed between the needle retainer 50 and the tip 22 so that fluid cannot leak out of the barrel between the tip 22 and the needle retainer 50. The needle retainer 50 has a bore for receiving the needle fitting 60. The fingers 54 have inwardly projecting latches engaging the rearward end of the needle fitting 60 to retain the needle against the rearward bias of the spring 75.

The needle fitting is a hollow substantially cylindrical element. The rearward end of the needle fitting 60 flares outwardly forming a generally frustoconical head. The frustoconical head mates with the inner surface of the fingers 54. Adjacent the frustoconical head 62 is an annular sealing rib 67 that protrudes from the surface of the needle fitting. The sealing rib 67 forms an interference fit with the inner bore of the needle retainer 50 to form a fluid-tight seal, as identified in FIG. 6 at "B", between the needle fitting 60 and the inner bore of the needle retainer. However, the interference fit between the sealing rib 67 and the needle retainer 50 is not sufficient to retain the needle against the rearward bias of the spring 75. The inner bore of the needle fitting forms a reservoir for receiving the rearward end of the needle and epoxy for bonding the needle to the needle fitting. The lowermost portion of the reservoir forms a plenum 63 in fluid communication with the needle 45. The reservoir is constricted forward of the plenum 63 to a diameter closely corresponding to the outer diameter of the needle. In this way, the constriction operates to center the needle within the reservoir.

A vent passage 64 in fluid communication with the plenum 63 extends through the width of the needle fitting head 62. The vent passage 64 provides fluid communication between the interior of the barrel 20 and the plenum 63. If the vent passage is aligned with the needle retainer fingers 54 so that the fingers overlap the vent passages, fluid flow through the vent passages will be either blocked or reduced. Accordingly, the fingers 54 should be located so that they do not overlap with the vent passages 64. Alternatively, and preferably, a circumferential vent groove 65 may be formed on the exterior surface of the needle fitting rearward of the sealing rib 67. The vent groove 65 intersects the vent passage 64 to form a fluid pathway around the fingers 54 to eliminate any problems associated with blockage of the vent passage 64 by the fingers. Configured in this manner, the fluid seal between the needle retainer and the barrel is immediately adjacent the fluid seal between the needle fitting and the needle retainer, and the fluid passage through the needle fitting and to the needle 45 is immediately rearward of the fluid seal between the needle fitting and the needle retainer. Since the fluid passage is immediately adjacent the rearward-most fluid seal, the space within the device in which air bubbles could potentially become trapped is minimized.

Figure 6:
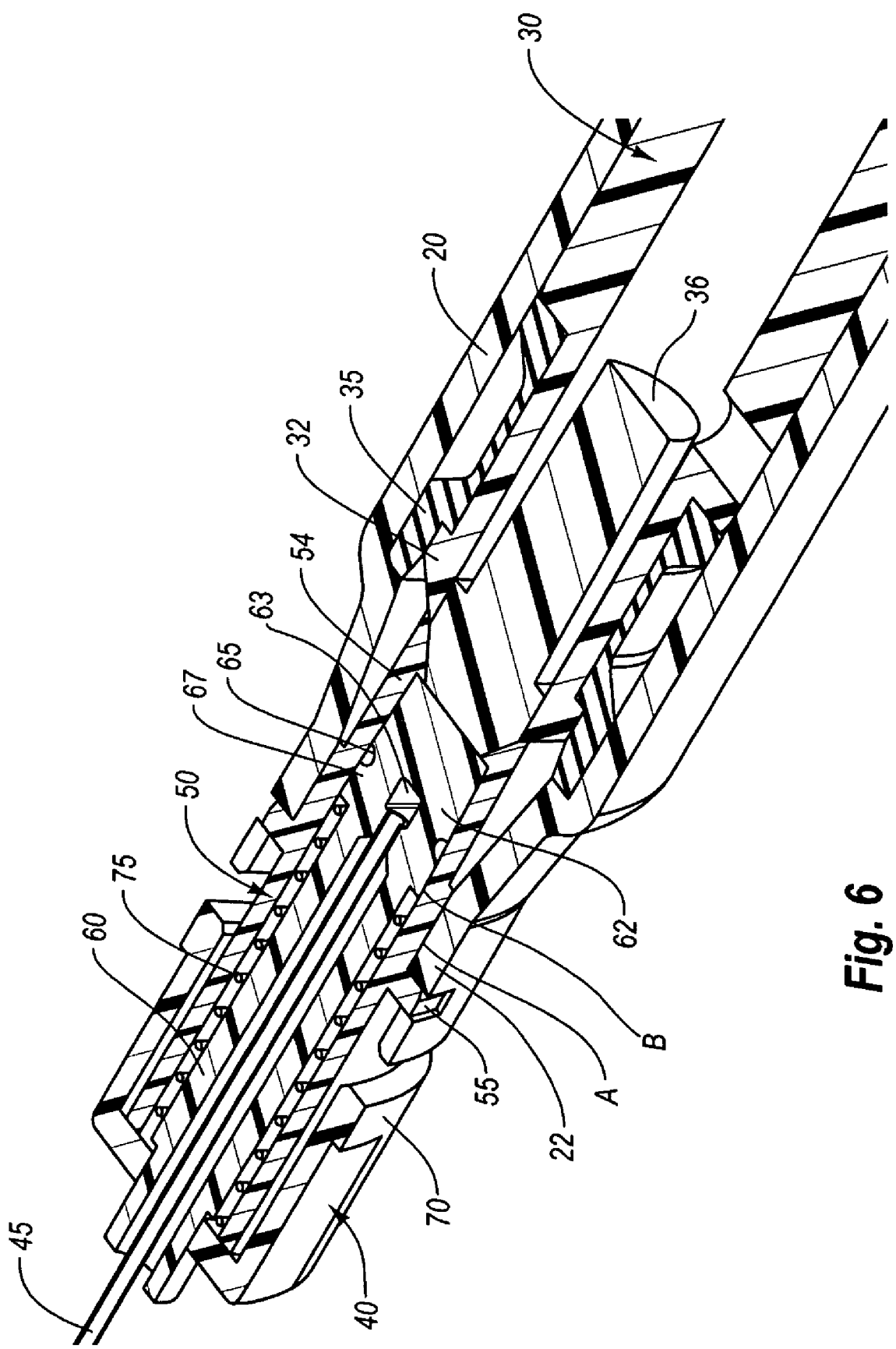
FIG. 6 is an enlarged fragmentary cross-sectional view of the forward end of the syringe illustrated in FIG. 1.
Figure 7:
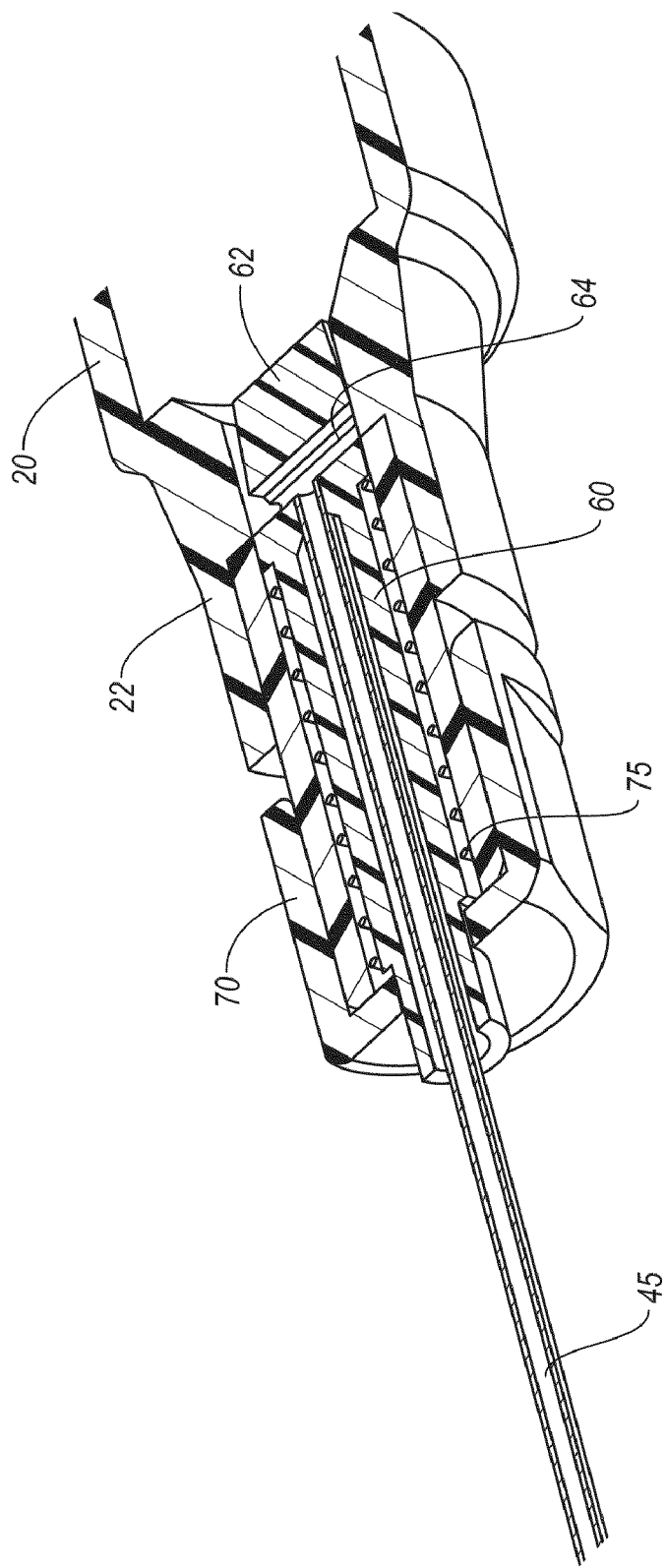
FIG. 7 is an enlarged fragmentary cross-sectional view of the forward end of the syringe illustrated in FIG. 1, orthogonal to FIG. 6.
Figure 9:
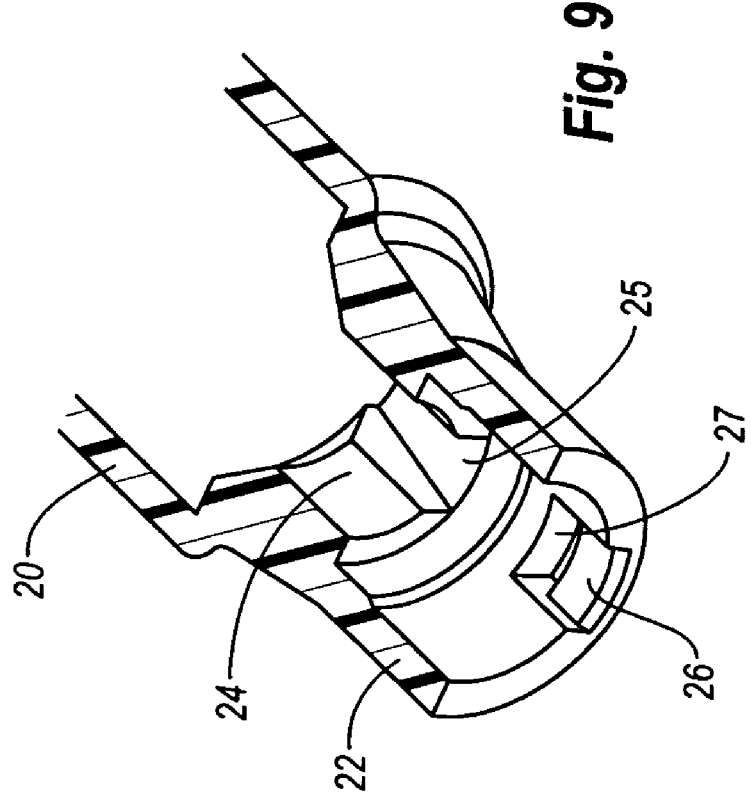
FIG. 9 is an enlarged fragmentary cross-sectional view of the forward end of the barrel of the syringe illustrated in FIG. 1, orthogonal to FIG. 8.
Figure 8:
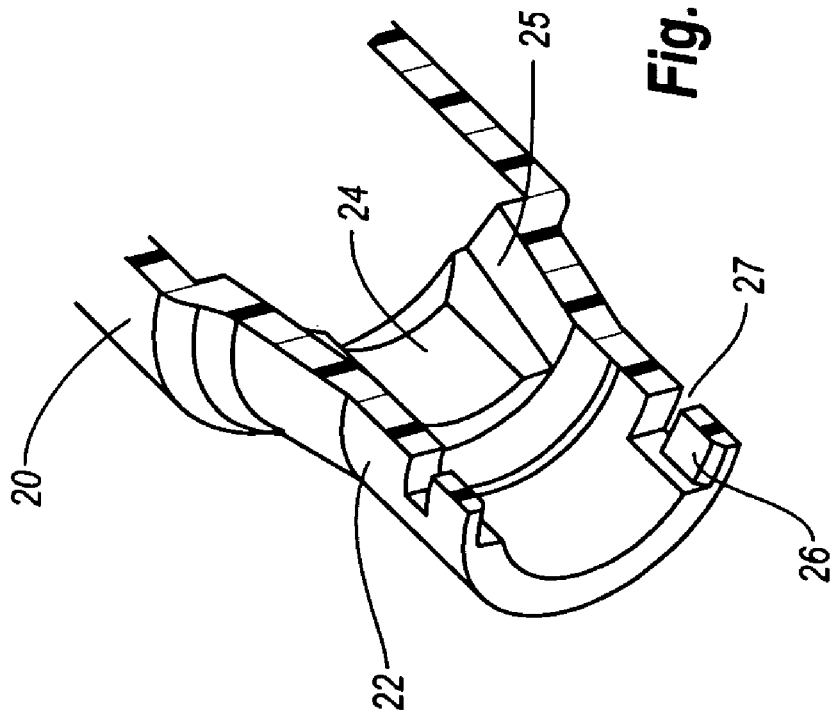
FIG. 8 is an enlarged fragmentary cross-sectional view of the forward end of the barrel of the syringe illustrated in FIG. 1.

The cap 70 is a hollow cylinder having a generally closed forward end with a reduced diameter opening. The forward end of the needle fitting 60 has a reduced diameter portion configured to project through the reduced diameter opening of the cap. A plurality of axially spaced circumferential ridges are formed on the interior surface of the cap. The cap ridges cooperate with a plurality of corresponding axially spaced circumferential locking ridges 56 on the exterior of the needle retainer 50. In this way, the cap and the needle retainer enclose the needle assembly 40 so that the needle assembly is a separable assembly that can be attached to the barrel 20. As shown in FIG. 6, the spring 75 is disposed within the needle retainer 50 circumscribing the needle fitting 60 bearing against the cap 70 and the head 62 of the needle fitting.

Referring again to FIG. 1, the tip 22 of the barrel 20 comprises a pair of locking windows 27 that cooperate with a pair of locking tabs 55 on the needle assembly 40 to attach the needle assembly to the barrel. The tip 22 includes a pair of axial alignment grooves 26 extending between the locking windows 27 and the forward end of the tip. The alignment grooves 26 are configured to receive the locking tabs 55 to provide proper alignment between the needle assembly 40 and the barrel 20 so that the locking tabs 55 are aligned with the locking windows 27.

The tip further comprises a pair of opposing clearance grooves 25 aligned with the needle retainer fingers 54. The clearance grooves 25 provide space for the outward radial displacement of the fingers 54. The tip 22 further includes a plurality of protrusions 24 projecting inwardly from the inner surface of the tip to fill the space adjacent the area in which the needle retainer fingers 54 are received. The protrusions 24 reduce the area between the fingers 54 and the interior of the tip, other than the clearance grooves 25 for the fingers. In this way the protrusions 24 substantially reduce the dead space between the needle retainer and the interior of the tip.

Configured in this manner, the device operates as follows. The needle assembly 40 is inserted into the tip 22 of the barrel so that the locking tabs 55 of the needle retainer 50 are aligned with the alignment grooves 26 of the tip. The needle assembly 40 is inserted into the tip until the locking tabs 55 engage the locking windows 27 to substantially permanently attach the needle assembly to the barrel 20.

The fluid is drawn into the barrel 20 by inserting the sharpened tip of the needle 45 into a fluid container and drawing the plunger 30 rearwardly. The needle 45 is then inserted into a patient and the fluid is injected into the patient by displacing the plunger 30 forwardly. At the end of the injection stroke, the head 33 of the plunger rod 32 engages the fingers 54 of the needle retainer 50 and the piston 35 engages the forward end of the barrel 20. Continued forward displacement of the plunger axially compresses the piston 35 and drives the frustoconical head of the plunger rod against the inwardly tapered surfaces of the fingers 54, thereby wedging the fingers apart. In other words, the plunger radially displaces the fingers outwardly. At the same time, the plug 36 that seals the opening at the forward end of the plunger engages the head 62 of the needle fitting 60, displacing the plug rearwardly into the cavity of the plunger so the plunger opening is not obstructed. Once the fingers 54 are displaced radially outwardly out of engagement with the needle fitting, the needle is released and the spring 75 propels the needle and attached needle fitting rearwardly into the cavity 38 in the plunger so that the sharpened tip of the needle is shielded against inadvertent contact.

The invention claimed is:

1. A safety medical device, comprising:
   a hollow barrel having an interior and terminating at a tip that defines a plurality of grooves radially spaced from each other;
   a needle having a sharpened tip operable between an extended position in which the needle is exposed for use and a retracted position in which the needle is shielded against inadvertent contact;
   a needle fitting connected with the needle, having a forward end and a rearward end, wherein the rearward end is closed;
   a spring biasing the needle toward the retracted position;
   a needle retainer releasably engaging the needle fitting via a plurality of retainer fingers to maintain the needle in the extended position;
   a fluid area having at least a portion between the forward and rearward ends of the needle fitting and the interior of the barrel, wherein the fluid area is in fluid communication with the needle, wherein the fluid area is positioned radially between the needle fitting and the interior of the barrel;
      wherein the needle retainer and the tip of the barrel are in contact with each other and form a fluid-tight seal;
      wherein the needle retainer and the needle fitting are separate components and form a fluid tight seal; and
   an actuator slidable within the barrel;
      wherein after use of the device, the actuator automatically engages the needle retainer to displace the plurality of retainer fingers into the plurality of grooves of the barrel tip and actuate retraction of the needle into the retracted position, and
      wherein the engagement of the actuator and the needle retainer permits the closed, rearward end of the needle fitting to be contacted without causing a structure to enter the needle fitting for fluid displacement.

2. The safety medical device of claim 1 wherein the actuator is a plunger operable to expel fluid from the barrel.

3. The safety medical device of claim 1 wherein the needle fitting includes a fluid passage so that the needle is in fluid communication with the interior of the barrel.

4. The safety medical device of claim 3 wherein the fluid-tight seal between the needle retainer and the tip of the barrel is adjacent the fluid-tight seal between the needle retainer and the needle fitting.

5. The safety medical device of claim 3 or 4 wherein an opening in the needle fitting is adjacent the fluid-tight seal between the needle retainer and the needle fitting.

6. The safety medical device of claim 2, wherein the barrel comprises a fluid cavity for receiving medicinal fluid, and the plunger is operable to expel fluid from the fluid cavity through the needle.

7. The safety medical device of claim 6 wherein the plunger comprises an axially compressible piston forming a fluid-tight seal with the interior of the barrel.

8. The safety medical device of claim 7 wherein continued forward displacement of the plunger after the plunger engages the needle retainer operates to axially compress the piston such that the needle retainer releases its engagement of the needle fitting to effectuate retraction of the needle.

9. A safety medical device, comprising:
a hollow barrel having a fluid cavity and a tip that comprises multiple inwardly projecting protrusions;
a needle assembly, comprising:
a needle having a sharpened tip;
a needle fitting attached to the needle, comprising an interior cavity forming a plenum, and a fluid passage between the plenum and the barrel fluid cavity in fluid communication with the barrel fluid cavity, wherein the needle and fluid passage are in fluid communication with the plenum;
a needle retainer comprising retainer fingers that are configured to releasably engage the needle fitting to retain the needle in a projecting position in which the sharpened tip projects forwardly from the barrel so that it is exposed for use,
wherein the needle retainer comprises a bore,
wherein the needle filling is a separate component with respect to the needle retainer and is disposed within the bore, forming a fluid-tight seal between the needle fitting and the bore, and
wherein the retainer fingers are configured to be displaced outwardly into areas between adjacent protrusions of the barrel tip to release the needle fitting;
a biasing element biasing the needle rearwardly into a retracted position in which the sharpened tip is shielded to prevent inadvertent contact with the sharpened tip; and
a plunger axially displaceable within the barrel to expel fluid from the barrel without causing a structure to enter the fluid passage and the interior cavity forming the plenum,
wherein the plunger comprises a hollow cavity for receiving the needle when the needle is displaced into the retracted position.

10. The safety medical device of claim 9 wherein the needle retainer comprises a pair of radially deformable latches engaging the needle fitting, and the plunger comprises an actuation surface operable to displace the latches radially thereby disengaging the needle fitting from the needle retainer.

11. The safety medical device of claim 9 wherein the barrel comprises a protrusion projecting radially inwardly adjacent the needle retainer to reduce the interior volume of the barrel between the needle retainer and the barrel.

12. The safety medical device of claim 11 wherein the needle retainer comprises a radially displaceable arm engaging the needle fitting, and the barrel comprises a channel aligned with the arm, adjacent the protrusion, for receiving the arm when the arm is displaced radially.

13. The safety medical device of claim 9 wherein the needle fitting comprises a circumferential groove intersecting the fluid passage.

14. The safety medical device of claim 9 wherein the needle retainer and the tip of the barrel form a fluid-tight seal.

15. The safety medical device of claim 14 wherein the fluid passage in the needle fitting comprises an inlet opening adjacent to, and rearward of, the seal between the needle retainer and the tip of the barrel.

16. The device of claim 9 wherein the needle fitting has a closed rearward end sealing the rearward end of the plenum.

17. A safety medical device, comprising:
a longitudinally elongated hollow barrel having a longitudinal axis and a fluid cavity and defining grooves adjacent to space-filling protrusions at an end thereof, wherein the grooves and the protrusions are alternatingly spaced around the barrel;
a needle assembly, comprising:
a needle having a sharpened tip;
a needle fitting attached to the needle, comprising an interior cavity forming a plenum, and a fluid passage transverse to the longitudinal axis and in fluid communication with the barrel fluid cavity, wherein the needle and fluid passage are in fluid communication with the plenum; and
a needle retainer releasably engaging the needle fitting to retain the needle in a projecting position in which the sharpened tip projects forwardly from the barrel so that it is exposed for use,
wherein the needle retainer comprises a bore,
wherein the needle fitting is a separate component with respect to the needle retainer and is disposed within the bore forming a fluid-tight seal between the needle fitting and the bore, and
wherein portions of the needle retainer are configured to be radially displaced into the grooves defined by the barrel;
a biasing element biasing the needle rearwardly into a retracted position in which the sharpened tip is shielded to prevent inadvertent contact with the sharpened tip; and
a plunger axially displaceable within the barrel to expel fluid from the barrel without causing a structure to enter the fluid passage and the interior cavity forming the plenum,
wherein the plunger comprises a hollow cavity for receiving the needle when the needle is displaced into the retracted position.

18. The safety medical device of claim 17 wherein the needle retainer comprises a pair of radially deformable latches engaging the needle fitting, and the plunger comprises an actuation surface operable to displace the latches radially thereby disengaging the needle fitting from the needle retainer.

19. The safety medical device of claim 17 wherein the barrel comprises a protrusion projecting radially inwardly adjacent the needle retainer to reduce the interior volume of the barrel between the needle retainer and the barrel.

20. The safety medical device of claim 18 wherein the needle retainer comprises a radially displaceable arm engaging the needle fitting, and the barrel comprises a channel aligned with the arm, adjacent the protrusion, for receiving the arm when the arm is displaced radially.

21. The safety medical device of claim 17 wherein the needle fitting comprises a circumferential grove intersecting the fluid passage.

22. The safety medical device of claim 17 comprising a seal between the needle retainer and the barrel, forming a fluid-tight seal.

23. The safety medical device of claim 21 wherein the fluid passage in the needle fitting comprises an inlet opening adjacent to, and rearward of, the seal.

24. The device of claim 17 wherein the needle fitting has a closed rearward end sealing the rearward end of the plenum.

* * * * *